(12) United States Patent
Jordan et al.

(10) Patent No.: US 8,133,285 B2
(45) Date of Patent: Mar. 13, 2012

(54) PERSONAL CARE COMPOSITIONS FOR COLORING HAIR

(75) Inventors: Susan L. Jordan, Doylestown, PA (US); Curtis Schwartz, Philadelphia, PA (US)

(73) Assignees: Union Carbide Chemicals & Plastics Technology LLC; Rohm and Haas Company

( * ) Notice: Subject to any disclaimer, the term of this patent is extended or adjusted under 35 U.S.C. 154(b) by 0 days.

(21) Appl. No.: 13/053,909

(22) Filed: Mar. 22, 2011

(65) Prior Publication Data

US 2011/0236334 A1    Sep. 29, 2011

Related U.S. Application Data

(60) Provisional application No. 61/317,754, filed on Mar. 26, 2010.

(51) Int. Cl.
*A61Q 5/10* (2006.01)

(52) U.S. Cl. .............. 8/405; 8/406; 8/408; 8/435; 8/552

(58) Field of Classification Search .............. 8/405, 406, 8/408, 435, 552
See application file for complete search history.

(56) References Cited

U.S. PATENT DOCUMENTS

| | | |
|---|---|---|
| 4,599,392 A | 7/1986 | McKinney et al. |
| 4,701,432 A | 10/1987 | Welborn, Jr. |
| 4,988,781 A | 1/1991 | McKinney et al. |
| 5,272,236 A | 12/1993 | Lai et al. |
| 5,322,728 A | 6/1994 | Davey et al. |
| 6,525,157 B2 | 2/2003 | Cozewith et al. |
| 6,960,635 B2 | 11/2005 | Stevens et al. |
| 2004/0231070 A1 * | 11/2004 | Morrissey et al. ................ 8/405 |

* cited by examiner

*Primary Examiner* — Eisa Elhilo

(57) ABSTRACT

Described are hair colorant compositions comprising an aqueous dispersion comprising an ethylene acrylic acid copolymer, and optionally a metallocene catalyzed polyolefin. an aqueous dispersion comprising a metallocene catalyzed polyolefin and an ethylene acrylic acid copolymer, and methods of reducing hair damage from hair colorants, comprising including an aqueous dispersion comprising a metallocene catalyzed polyolefin and an ethylene acrylic acid copolymer in the hair colorant.

13 Claims, No Drawings

PERSONAL CARE COMPOSITIONS FOR COLORING HAIR

CROSS-REFERENCE TO RELATED APPLICATION

This application claims benefit of priority from U.S. Provisional Pat. App. No. 61/317,754, filed Mar. 26, 2010, which application is incorporated by reference herein in its entirety.

FIELD

The present application relates to personal care compositions.

BACKGROUND

"Permanent" hair color products and lighteners typically work by lightening the hair's natural pigment (melanin), and then replacing the melanin with the desired shade of color. The color is often achieved through oxidizable dye intermediates (typically para- and ortho-aromatic diamines, which are readily oxidized and are necessary for the dark shades and depth of color) and preformed dyes or tints. A developer (oxidizing agent, usually peroxide based) is used to strip away natural pigment and to activate the dyes and couplers. An alkalizing agent (usually an ammonia solution) also reacts with the dye intermediates to help impart the desired color. To prevent premature reaction, the developer is typically isolated in a separate bottle from the alkalizing agent.

Both peroxides and ammonia compounds are known to damage hair, and their reaction swells the hair cuticle, permitting the color to enter the cortex, but also understandably rendering the hair more fragile. Current cationic conditioners are incompatible with hair dye formulations. As can be appreciated, it is a major challenge in the art to create as little damage to the hair as possible while coloring it. At the same time, it is incredibly important not to affect the complex color reactions necessary to achieve the exact desired color.

SUMMARY

In one embodiment, the present invention provides hair colorant compositions, comprising an aqueous dispersion comprising an ethylene acrylic acid copolymer, and optionally, a metallocene catalyzed polyolefin.

DETAILED DESCRIPTION

In one embodiment, the present invention provides hair colorant compositions, comprising an aqueous dispersion comprising an ethylene acrylic acid copolymer, and optionally a metallocene catalyzed polyolefin.

In the broadest embodiment of the present invention, "hair colorant" is intended to have its literal meaning, however, in a preferred embodiment, the hair colorant is used in personal care. "Personal care" relates to compositions to be topically applied to a person (i.e., not ingested). Preferably, the personal care composition is cosmetically acceptable. "Cosmetically acceptable" refers to ingredients typically used in personal care compositions, and is intended to underscore that materials that are toxic when present in the amounts typically found in personal care compositions are not contemplated as part of the present invention.

In one embodiment, the hair colorant is a temporary, semi-permanent, demi-permanent, or permanent hair colorant. "Temporary" hair colorant refers to pigments that do not penetrate the cuticle layer of hair, but merely adsorb to the hair shaft. Temporary hair colorant is typically removed with a single shampooing. "Semi-permanent" hair colorant uses smaller pigment molecules that partially penetrate the hair shaft. For this reason, the color will typically last 4-5 shampoos. "Demi-permanent" hair colorant is permanent hair color that contains an alkaline agent other than ammonia (e.g., ethanolamine, sodium carbonate) and, while always employed with a developer, the concentration of hydrogen peroxide in that developer may be lower than used with a permanent hair color. Because there is essentially no lifting (i.e., removal) of natural hair color, demi-permanent colorants cannot lighten hair, and usually persist for more than 20 shampoos. "Permanent" hair colorants contain a developer (oxidizing agent), dyes, couplers, and ammonia (alkalizing agent). When the alkalizing ingredient is combined with the developer, the chemical reaction swells the hair permitting the color to enter the cortex. The melanin is also partially removed and subsumed by the new color.

Permanent color is truly permanent and will not wash out, although it may fade. Permanent color is the only way to dye dark hair into a lighter shade, and it must be done stepwise, first, the hair is lightened, then color is applied.

In one embodiment, the hair colorant is a permanent hair colorant, and the aqueous dispersion is mixed with an oxidizing agent. In a preferred embodiment, however, the hair colorant is a permanent hair colorant, and the aqueous dispersion is mixed with an alkalizing agent. As the primary intermediate and/or couplers are included with the alkalizing agent, the aqueous dispersion can be said to be mixed with the primary intermediate and/or couplers.

Those skilled in the art are aware of the identities of conventional oxidizing agents, alkalizing agents, primary intermediates, couplers, and additional ingredients for hair colorants. A particularly preferred conventional hair colorant is L'OREAL SUPERIOR PREFERENCE hair colorants, commercially available from L'Oreal (France).

Copolymerizing ethylene with acrylic acid yields ethylene-acrylic acid (EAA) copolymers, which are known as flexible thermoplastics for blister packaging and the like. A preferred ethylene acrylic acid copolymer comprises greater than about 15 wt % acrylic acid, preferably greater than about 17 wt % acrylic acid, more preferably about 20 wt % acrylic acid. It should be understood that ranges recited in this disclosure include all subcombinations of ranges.

A preferred EAA copolymer is PRIMACOR 5990 copolymer (20 wt % acrylic acid), which has a melt index of 1300 g/10 minute (ASTM Method D-1238 at 190° C.) and a Brookfield viscosity of 13,000 cps at 350° F., and is available from The Dow Chemical Company. Another preferred EAA copolymer is PRIMACOR 5980i copolymer (20.5 wt % acrylic acid), which has a melt index of 300 g/10 minute (ASTM Method D-1238 at 190° C.), available from The Dow Chemical Company. EAA copolymers are also available under the tradename NUCREL 2806, available from E.I. du Pont de Nemours and Company, Inc. Ethylene-acrylic acid and ethylene-methacrylic acid copolymers, are described in U.S. Pat. Nos. 4,599,392, 4,988,781, and 5,938,437, each of which is incorporated herein by reference in its entirety.

Metallocene catalyzed polyolefins are polyolefins produced with a metallocene catalyst as described in U.S. Pat. Nos. 4,701,432, 5,322,728, and 5,272,236, each of which is incorporated herein by reference in its entirety. As a specific embodiment of the present invention, the metallocene catalyzed polyolefins are polyethylenes produced with a metallocene catalyst. Such metallocene catalyzed polyethylenes are available e.g. from The Dow Chemical Company under the trademark AFFINITY or ENGAGE (ethylene/octene copolymers) and from Exxon Chemical Company under the trademark EXACT (ethylene/butene copolymers, ethylene/hexene copolymers, or ethylene/butene/hexene terpolymers). In one embodiment, the metallocene catalyzed polyolefin is at least one of ethylene/octene copolymers, ethylene/butene copolymers, ethylene/hexene copolymers, ethylene/propylene or ethylene/butene/hexene terpolymers, preferably an ethylene octene copolymer. In another embodiment, the metallocene catalyzed polyolefin is a propylene/alpha-olefin copolymer, which is further described in details in the U.S. Pat. Nos. 6,960,635 and 6,525,157, each of which is incorporated herein by reference in its entirety. Such propylene/alpha-olefin copolymers are commercially available from The Dow Chemical Company, under the tradename VERSIFY™, or from ExxonMobil Chemical Company, under the tradename VISTAMAXX™.

In one embodiment, the ethylene acrylic acid copolymer and metallocene catalyzed polyolefin are melt-kneaded in an extruder along with water and a neutralizing agent, such as ammonia, potassium hydroxide, or a combination of the two, to form an aqueous dispersion.

Mechanical dispersion, such as a Parr reactor, is used to create the aqueous dispersion.

In one embodiment, the metallocene catalyzed polyolefin comprises at least one of ethylene/octene copolymers, ethylene/butene copolymers, ethylene/hexene copolymers, or ethylene/butene/hexene terpolymers, preferably a ethylene octene copolymer.

The ethylene acrylic acid copolymer is present in a range from about 2 wt % to about 35 wt % by weight of the aqueous dispersion, preferably in a range from about 4 wt % to about 20 wt %.

In one embodiment, the metallocene catalyzed polyolefin is present in a range from about 10 wt % to about 50 wt % by weight of the aqueous dispersion, preferably in a range from about 15 wt % to about 40 wt %.

Typically, the ethylene acrylic acid copolymer and metallocene catalyzed polyolefin is in a polymer ratio of about 40:60 to about 15:85.

The solids content of the aqueous dispersion is in a range from about 10% by weight to about 50% by weight, preferably about 40% by weight.

In turn, the aqueous dispersion is present in a range from about 0.5 wt % to about 10 wt % of solids, preferably about 1 wt % to about 5 wt %, by weight of the personal care composition.

The amount of optional ingredients effective for achieving the desired property provided by such ingredients can be readily determined by one skilled in the art.

In one embodiment, the present invention provides methods of reducing hair damage from hair colorants, comprising including an aqueous dispersion comprising a metallocene catalyzed polyolefin and an ethylene acrylic acid copolymer in the hair colorant.

In use, the hair colorant compositions are applied to hair in a conventional manner.

EXAMPLES

The following examples are for illustrative purposes only and are not intended to limit the scope of the present invention. All percentages are by weight unless otherwise specified.

Example 1

Personal care compositions of the present invention include aqueous dispersions comprising an ethylene acrylic acid copolymer. Examples of such aqueous dispersions include the following:

Batch 1

A 41.7% solids aqueous dispersion of ethylene acrylic acid and metallocene catalyzed polyolefin, commercially available from The Dow Chemical Company under the tradename HYPOD 8510, produced using Dow's BLUEWAVE technology.

Batch 2

PRIMACOR 5980i 20% ethylene acrylic acid resin (60 g), potassium hydroxide (25 g of 30 wt. %), and water (21 g) are placed in a 300 mL Parr reactor vessel fitted with a Cowles blade. The material is heated to 120° C. while mixing slowly. Once the set temperature is reached, the mixer is run on high (~1800 rpm) for 25 minutes. While still mixing on high, the sample is diluted with water fed into the reactor with an HPLC pump at a rate of 40 mL/min to the desired concentration of 25.7% solids by weight based on the amount of ethylene acrylic acid resin. Heat is removed and stirring continues until the temperature cools to at least 45° C. The Parr is then opened and the dispersion is collected.

Example 2

Exemplary hair colorants of the present invention contain the components recited in TABLE 1 on a weight/weight basis (wt. %).

TABLE 1

|  | Batch A | Batch A | Batch B | Batch B |
| --- | --- | --- | --- | --- |
| L'Oréal Superior Preference 6 AM Light Amber Brown (warmer) | 142 g | 97% | 142 g | 96.1% |
| Batch 1 (41.7%) | 3.5 g | 1.0% active polymer | — | — |
| Batch 2 (25.7%) | — | — | 5.7 g | 1.0% active polymer |

To the bottle marked "Color Gel," add component substantially similar to Batch 1 or Batch 2 to achieve a final concentration of 1% Batch 1 or 1% Batch 2.

Example 3 (Comparative)

Conventional hair colorants compositions contain the components recited in TABLE 2 on a weight/weight basis (wt. %).

TABLE 2

|  | Comp. Batch Z | Comp. Batch Z |
| --- | --- | --- |
| L'Oréal Superior Preference 6 AM Light Amber Brown (warmer) | 142 g | 96.1% |
| Deionized water | 5.7 g | 3.9% |

The procedure of Example 2 is used, except Batch 1 or Batch 2 is replaced with an equal amount of water.

Example 4

Compositions substantially according to the protocols of Examples 2 and 3 were prepared. Pre-washed and dried tresses of European 8-hour bleached hair and European virgin brown hair (medium)(both available from International Hair Importers and Products Inc.) were treated with about 1.5 g of dye mix brushed in for approximately one minute. The tress is then squeezed and flipped over, with about 1 g of dye mix brushed in to other side of the tress. The tress is then hung for about 30 minutes to allow the dye to set.

The hair tresses were hung for wet sensory evaluation study. Two expert panelists trained to evaluate the performance of cosmetic products on hair were asked to evaluate comb-ability and feel in the wet stage. Each panelist evaluated fifteen tresses, five tresses treated with a composition of Batch A of the present invention, five tresses treated with a composition of Batch B of the present invention, and five tresses treated with a comparative composition Comparative Batch Z. The panelists were asked to rate each tress from 1-5 (5 being best). Results are reported in TABLE 3.

TABLE 3

|  | Batch A | Batch B | Comparative Batch Z |
|---|---|---|---|
| Wet comb - Brown | 4.9 ± 0.32 | 4.9 ± 0.32 | 3.2 ± 0.63 |
| Wet feel - Brown | 4.7 ± 0.48 | 4.7 ± 0.48 | 2.9 ± 0.88 |
| Wet comb - Bleached | 3.3 ± 0.48 | 3.4 ± 0.52 | 1.7 ± 0.48 |
| Wet feel - Bleached | 3.8 ± 0.42 | 3.8 ± 0.42 | 1.7 ± 0.67 |

As can be appreciated, the compositions of the present invention significantly improve wet combability and wet feel in hair containing dye compositions.

Next, the tresses are rinsed by adding water, working into a lather for about 30 seconds, and rinsing under about 38° C. running water for approximately one minute, with several squeezing and flipping procedures. Immediately after rinsing, the panelists were again asked to rate each tress from 1-5 (5 being best). Results are reported in TABLE 4.

TABLE 4

|  | Batch A | Batch B | Comparative Batch Z |
|---|---|---|---|
| Wet comb - Brown | 3.2 ± 0.79 | 3.6 ± 0.52 | 1.6 ± 0.52 |
| Wet feel - Brown | 3.3 ± 0.48 | 3.8 ± 0.42 | 1.9 ± 0.57 |
| Wet comb - Bleached | 2.9 ± 0.74 | 2.7 ± 0.48 | 1.5 ± 0.71 |
| Wet feel - Bleached | 3.0 ± 0.47 | 2.3 ± 0.48 | 1.4 ± 0.70 |

As can be appreciated, the compositions of the present invention significantly improve wet combability and wet feel in rinsed dyed hair.

It is understood that the present invention is not limited to the embodiments specifically disclosed and exemplified herein. Various modifications of the invention will be apparent to those skilled in the art. Such changes and modifications may be made without departing from the scope of the appended claims.

Moreover, each recited range includes all combinations and subcombinations of ranges, as well as specific numerals contained therein. Additionally, the disclosures of each patent, patent application, and publication cited or described in this specification are hereby incorporated by reference herein, in their entireties.

The invention claimed is:

1. A hair colorant composition, comprising an aqueous dispersion comprising an ethylene acrylic acid copolymer.

2. The hair colorant composition of claim 1, wherein the aqueous dispersion further comprises a metallocene catalyzed polyolefin.

3. The hair colorant composition of claim 1, wherein the hair colorant is a temporary, semi-permanent, demi-permanent, or permanent hair colorant.

4. The hair colorant composition of claim 1 or 2, wherein the hair colorant is a permanent hair colorant.

5. The hair colorant composition of claim 4, wherein the aqueous dispersion is mixed with an oxidizing agent.

6. The hair colorant composition of claim 4, wherein the aqueous dispersion is mixed with an alkalizing agent.

7. The hair colorant composition of claim 4, wherein the aqueous dispersion is mixed with at least one primary intermediate or coupler.

8. The hair colorant composition of claim 1, wherein the metallocene catalyzed polyolefin comprises at least one of ethylene/octene copolymers, ethylene/butene copolymers, ethylene/hexene copolymers, or ethylene/butene/hexene terpolymers, preferably a ethylene octene copolymer.

9. The hair colorant composition of claim 1, wherein the ethylene acrylic acid copolymer is present in a range from about 2 wt % to about 35 wt % by weight of the aqueous dispersion.

10. The hair colorant composition of claim 1, wherein the metallocene catalyzed polyolefin is present in a range from about 10 wt % to about 50 wt % by weight of the aqueous dispersion.

11. The hair colorant composition of claim 1, wherein the aqueous dispersion is present in a range from about 0.5 wt % to about 10 wt % by weight of the hair colorant composition.

12. A method of reducing hair damage from hair colorants, comprising including an aqueous dispersion comprising an ethylene acrylic acid copolymer in the hair colorant.

13. A method of reducing hair damage from hair colorants, comprising including an aqueous dispersion comprising a metallocene catalyzed polyolefin and an ethylene acrylic acid copolymer in the hair colorant.

* * * * *